US006451551B1

(12) United States Patent
Zhan et al.

(10) Patent No.: US 6,451,551 B1
(45) Date of Patent: Sep. 17, 2002

(54) RELEASING EMBEDDING MEDIA FROM TISSUE SPECIMENS

(75) Inventors: Guangrong Zhan, Shrewsbury, MA (US); Krishan L. Kalra, Danville, CA (US); Sheng-Hui Su; Taiying Chen, both of San Ramon, CA (US)

(73) Assignee: BioGenex Laboratories, San Ramon, CA (US)

( * ) Notice: Subject to any disclaimer, the term of this patent is extended or adjusted under 35 U.S.C. 154(b) by 0 days.

(21) Appl. No.: 09/573,073

(22) Filed: May 16, 2000

Related U.S. Application Data

(63) Continuation of application No. 08/212,175, filed on Mar. 11, 1994.

(51) Int. Cl.$^7$ ................................................. G01N 1/30
(52) U.S. Cl. ................................. 435/40.52; 435/40.5
(58) Field of Search ........................... 435/40.52, 40.5; 83/856, 915.5; 422/61; 427/2.11; 436/174, 176

(56) References Cited

U.S. PATENT DOCUMENTS

| 4,530,781 A | * | 7/1985 | Gipp | 252/546 |
| 4,839,194 A | * | 6/1989 | Malluche et al. | 427/2 |
| 4,911,915 A | * | 3/1990 | Fredenburgh | 424/3 |
| 5,124,062 A | * | 6/1992 | Stevens | 252/162 |
| 5,355,439 A | * | 10/1994 | Bernstein et al. | 395/82 |
| 5,578,452 A | * | 11/1996 | Shi et al. | 435/7.21 |
| 6,207,408 B1 | * | 3/2001 | Essenfeld et al. | 435/40.5 |

FOREIGN PATENT DOCUMENTS

| DE | 354322 A1 | * | 6/1987 |
| WO | WO 9524498 A | * | 9/1995 |

* cited by examiner

*Primary Examiner*—Ralph Gitomer
(74) *Attorney, Agent, or Firm*—James C. Weseman, Esq.; The Law Offices of James C. Weseman

(57) ABSTRACT

Releasing the embedding medium from an embedded histochemically reactive tissue specimen is provided by contacting the embedded tissue specimen with a releasing composition under conditions sufficient to release a sufficient portion of the embedding medium associated with the histochemically reactive tissue specimen to permit analysis without substantial adverse effect on the histochemical reactivity of the specimen.

20 Claims, No Drawings

RELEASING EMBEDDING MEDIA FROM TISSUE SPECIMENS

This application is a continuation of Ser. No. 08/212,175 filed Mar. 11, 1994.

TECHNICAL FIELD

The present invention relates to methods and compositions for releasing embedded tissue specimens from the embedding medium.

BACKGROUND OF THE INVENTION

Paraffin has been used for many years as an embedding medium in techniques for the preparation of tissue specimens for sectioning in a microtome to produce specimen sections for histological studies. Such embedding techniques generally include the well known steps of specimen fixation, dehydration, clearing, paraffin infiltration or impregnation, blocking or embedding in a block of paraffin, slicing the block and specimen into thin sections, mounting the sections on slides, removing the paraffin and solvents employed for this purpose (commonly termed "deparaffinizing"), rehydration of tissue sections and staining the sections prior to analysis.

The primary purpose of the embedding medium is to permit the specimens to be sectioned and mounted in an approximation of the natural state. Plastic resins have also been used as embedding medium to provide a harder specimen that allows the cutting of thinner sections. However, the use of paraffin-embedding has the advantage that the wax can be dissolved away from specimens prior to staining, allowing sections to be stained in the form of naked slabs of biopolymer and avoiding the extra difficulties and artifacts associated with the presence of unremovable resin-embedding medium (Horobin, R. W., In "*Histochemical and Immunochemical Techniques: Application to pharmacology and toxicology*" (1991) Bach, P. and Baker, J., eds., Chapman & Hall, New York, N.Y., pp. 1–9).

Recent improvements in paraffin-embedding compositions have broadened the applicability of the technique while maintaining its compatibility with downstream manipulation and analysis of samples. For example, an improved paraffin-based embedding material, which includes a mixture of paraffin and an effective amount of ethylene-vinyl acetate copolymer (0.5% to 5% by weight of paraffin) is reported to allow shorter infiltration time and thinner sections (U.S. Pat. No. 4,497,792). Another improvement, the double-embedding technique, yields sections of tissue membranes that usually measure only 10 microns in thickness. In this method, several membranes are fixed and mounted on needles located at the bottom of a plastic box and then embedded in agarose. The agarose block is removed, dehydrated in alcohol, cleared with HistoPetrol (trade name for a mixture of isoparaffin hydrocarbons), permeated with paraffin and sectioned. The observed tissue morphology is comparable to that obtained with methacrylate plastic embedding but is less time-consuming, less hazardous since no plastic hardener and activator are used, and makes immunohistochemical studies easier (Ghassemifar, R. et al. "A double-embedding technique for thin tissue membranes" *Biotech. Histochem.* 67:363–366 (1992)). Consequently, deparaffmization of fixed, e.g. formalin fixed, paraffin-embedded tissue sections is still a widely used methodology, particularly in hospital histopathology laboratories for immunodiagnostic purposes.

Xylene, which is a flammable, volatile and toxic organic solvent, is commonly used in protocols to solubilize paraffin for deparaffinization of specimen sections. Typically, the microscope slide-mounted specimen is immersed in a xylene bath until the paraffin is solubilized. The treated specimen is then washed with a series of alcohol solutions of decreasing alcohol concentration, typically as baths in which the specimen is immersed, to remove xylene before a final wash with water. Efforts have been made to replace xylene in the deparaffinization technique with less toxic and less volatile solvents (Mullin, L. S. et al. "Toxicology update isoparaffmic hydrocarbons: A summary of physical properties, toxicity studies and human exposure data" *J. Appl. Toxicol.* 10:135–142 (1990)). Terpene oil (e.g. available under the trade name AmeriClear from Baxter Health Care Diagnostics, Inc., McGaw Park, Ill.) and isoparaffinic hydrocarbons (e.g. available under the trade name Micro-Clear from Micron Diagnostics, Inc., Fairfax, Va.) produced equal deparaffinization compared to xylene (Jones, R. T. et al. "Comparison of deparaffinization agents for an automated immunostainer" *J. Histotechnology* 16:367–369 (1993)). However, a series of alcohol washes were still required to remove either solvent prior to the water wash to achieve compatibility with most types of staining, particularly immunohistochemical staining.

Furthermore, the use of paraffin-embedded specimens with automated systems, such as automated immunostaining devices, is increasing. In these applications, the complexity of the multiple manipulations necessitated by conventional deparaffinization methodology creates a substantial obstacle to the efficient, cost-effective and reproducible handling of embedded tissue specimens.

Accordingly, there remains a need for compositions and methods that can effectively remove, or otherwise eliminate, paraffin, improved paraffin-based and other embedding materials from specimens prior to histochemical or other diagnostic analyses, while minimizing danger to users, allowing compatibility with automated systems, and maintaining compatibility with downstream analyses. Compositions and methods that entail no or limited toxicity or carcinogenicity, produce no or minimal odors, reduce the quantity of toxic solvents used, minimize hazardous wastes, and/or decrease corrosiveness and inflammability are desirable. One such composition and method which has found use is disclosed in PCT Publication WO95/24498, published on Sep. 14, 1995. However, it remains desirable to minimize the use of organic solvents, even those having minimal toxicity or carcinogenicity, odors, hazardous waste concerns, corrosiveness and inflammability.

DISCLOSURE OF THE INVENTION

The present invention provides methods and compositions for releasing the embedding medium from embedded histochemically reactive tissue specimens prior to histochemical or other analyses. In one aspect, the invention provides a method comprising contacting the embedded tissue specimen with a releasing composition comprising a non-polar organic solvent, a polar organic solvent, a surfactant, and water, under conditions sufficient to release a sufficient portion of the embedding medium associated with the histochemically reactive tissue specimen to permit analysis without substantial adverse effect on the histochemical reactivity of the specimen.

The methods provided can effectively remove or otherwise eliminate embedding media, and particularly wax or modified wax-based embedding media, more particularly paraffin or paraffin-based media, from tissue specimens prior to histochemical or other analyses, while minimizing danger to users, allowing compatibility with automated use, and maintaining compatibility with downstream analyses. In this regard, it is considered important to release a portion of the embedding medium associated with the tissue specimen without substantial adverse effect on the histochemical reactivity of the specimen.

The present methods entail no known toxicity or carcinogenicity, no noxious or toxic odors, reduce the quantity of toxic solvents used, minimize hazardous wastes, and/or decrease corrosiveness and inflammability. The methods are especially useful for eliminating the use of xylene and for reducing the use of alcohol in preparation of tissue sections for histochemical staining, particularly in hospital laboratories. Compositions and kits for releasing the embedding medium from an embedded specimen are also provided. The composition comprises a non-polar organic solvent, a polar organic solvent, a surfactant, and water, and the kit comprises a releasing composition of the invention and a second composition of (1) a histochemical staining reagent or (2) an aqueous wash solution for removing, or otherwise eliminating, residual releasing solution.

Other aspects of the present invention will be readily apparent from the following more detailed description.

DETAILED DESCRIPTION OF THE INVENTION

The present invention provides methods and compositions for releasing the embedding medium from embedded histochemically reactive tissue specimens prior to histochemical or other analyses such as immunohistochemistry and in situ hybridization, special stains and classical dye stains. In one aspect, the invention provides a method comprising contacting the embedded tissue specimen with a releasing composition comprising a non-polar organic solvent, a polar organic solvent, a surfactant, and water, under conditions sufficient to release a sufficient portion of the embedding medium associated with the histochemically reactive tissue specimen to permit analysis without substantial adverse effect on the histochemical reactivity of the specimen.

The present invention eliminates or minimizes the use of xylene or xylene-substitute solvents in histological laboratories. The compositions and methodology described herein effectively remove, or otherwise eliminate, paraffin or other wax residue from tissue sections and have no adverse effect on the quality or histochemical reactivity of tissue sections prepared for histochemistry and in situ hybridization. Application of this methodology can be extended to other analytical applications where removal of embedding medium from tissue sections are desired, such as in situ hybridization, classical dye stains and special stains.

In one aspect, the present invention employs new releasing compositions for releasing embedding media, and particularly wax or modified wax-based embedding media, particularly paraffin or paraffin-based, from tissue specimens prior to histochemical or other analyses, while minimizing danger to users, allowing compatibility with automated use, and maintaining compatibility with downstream analyses. In this regard, it is considered important to release a portion of the embedding medium associated with the tissue specimen without substantial adverse effect on the histochemical reactivity of the specimen. In further embodiments the composition of the invention may optionally be diluted with water.

By "embedding medium" is meant any composition that is used in the histochemical art for embedding or otherwise supporting histochemically reactive tissue specimens for histochemical or other analyses, such as immunohistochemistry and in situ hybridization, special stains and classical dye stains. As one example of an embedding medium, wax is often used for this purpose.

By "wax" is meant a composition used in the histochemical art for embedding histochemically reactive specimens for histochemical or other analyses that is typically solid at room temperature, usually consists of a complex mixture of higher hydrocarbons often including esters of higher fatty acids and higher glycols, can be mineral, natural or synthetic in origin, is harder and more brittle than fats, is soluble in oils and fats, and can optionally contain additives that enhance its specimen-embedding properties. Paraffin is an example of a mineral wax most commonly used in the histochemical field. Paraffin is typically prepared by distillation of petroleum, and is a mixture of primarily solid saturated hydrocarbons.

By "histochemical" is meant generally the chemical analysis of tissue specimens for morphological, genetic or other characteristics, and is meant to include, but not be limited to, the techniques and methods known as immunohistochemical, cytochemical, histopathologic, hematoxylin and eosin (H&E) staining, enzyme histochemical, special stain, micro technique, in situ hybridization, and the use of molecular probes. Texts illustrating histochemical techniques include "Histochemical and Immunochemical Techniques: Application to pharmacology and toxicology," (1991) Bach, P. and Baker, J., eds., Chapman & Hall, New York, N.Y. pp. 1–9, and in "Stains and Cytochemical Methods," (1993) M. A. Hayat, ed., Plenum Press, New York, N.Y.

By "releasing the embedding medium" is meant removing or otherwise eliminating a sufficient amount of the embedding medium associated with a tissue specimen so as to permit the histochemically reactive tissue specimen to be subjected to analysis. Typically, such analysis is histochemical, and the amount of the embedding medium which should be removed will be the amount sufficient to permit the analysis technique of choice to gain access to at least one of the histochemically reactive sites in the histochemically reactive tissue specimen.

By "histochemically reactive tissue specimen" is meant a sample of animal or plant cells or tissues which is selected and treated so as to preserve a detectable amount of the native histochemical reactivity inherent in the sampled organism prior to the sampling. Typically, such specimens are obtained as tissue sections by biopsy, necropsy, and the like, in accordance with techniques know in the histochemical arts.

Because the present compositions are typically prepared by combining components without a precise determination of the final volume of the composition or accounting for volume changes upon mixing, the percentages for each component are qualified with the term "about" or "approximately," with the understanding that one skilled in the art would appreciate the imprecision of the values as a consequence of composition preparation; however, preferably, percentage values are taken to mean their precise value when volume changes upon mixing are taken into account.

In accordance with the invention, the non-polar organic solvent is a hydrocarbon or mixture of hydrocarbons (e.g. as from a petroleum distillate) that has a boiling point well above room temperature, preferably above 110° C., more preferably from about 140° C. to about 250° C., that is in liquid phase at the temperatures used with the present invention (usually 5° to 100° C.), and that is capable of dissolving or otherwise releasing the embedding medium used for embedding biological specimens. The present non-polar solvent can be a complex mixture of long-chain linear and branches alkane hydrocarbons containing, for example, esters of fatty acids and higher glycols. As a representative example for releasing an embedding medium, the paraffin solubility of the solvent at 25° C. is typically at least 0.1 gram of paraffin per liter of solvent, preferably 0.1 gram per 100 mL of solvent, more preferably 0.1 gram per 10 mL of solvent, and most preferably capable of a dissolving an amount of paraffin equal to about 50% of the solvent solutions weight. The non-polar solvent is further desirably miscible with a polar organic solvent when used in a composition of the invention. Examples of non-polar organic solvents include aromatic hydrocarbons, aliphatic hydrocarbons, terpenes, other oils, and petroleum distillates. Preferred non-polar organic solvents have little or no toxic effects. Furthermore preferred solvents are those not classified by the Environmental Protection Agency as hazardous waste. A preferred non-polar solvent furthermore has a flash point higher than about 60° C. which minimizes flanmmability. A preferred solvent also lacks carcinogenicity and corrosiveness. An isoparaffinic hydrocarbon is an example of a preferred non-polar solvent, in part because of its lack of toxicity, carcinogenicity, corrosiveness and flammability (Mullin et al. 1990). Preferred isoparaffins are branched aliphatic hydrocarbons with a carbon skeleton length ranging from approximately $C_{10}$ to $C_{15}$, or mixtures thereof. One preferred isoparaffin hydrocarbon mixture has a flashpoint of about 74° C. Another preferred non-polar solvent is a mixture of $C_{10}$ to $C_{50}$ branched or linear hydrocarbon chains having a distillation range from a boiling point of 150° C. to about 250° C., and has the general formula of $C_nH_{(2n\pm m)}$ where n=10–50 and m=0–4. Mineral spirits is another preferred non-polar organic solvent. A preferred terpene is limonene. Other terpenes that can be used include terpinenes and terpineols. Less preferably, the solvent is an aromatic hydrocarbon solvent such as an alkyl benzene, e.g. xylene, or dialkylbenzene, e.g. toluene. Toluene and xylene are less preferred because of their toxicity and rating as hazardous waste. Furthermore, as discussed below, even when xylene or toluene are used in embodiments of the invention, subsequent alcohol washes are eliminated and replaced with a non-hazardous aqueous wash solution. In certain embodiments of the invention, the aqueous wash solution can simply include water, in alternative embodiments the solution will contain buffer, salts or other reagents useful for solubilization or releasing of the embedding medium, washes, or subsequent histochemical steps, so long as such optional ingredients or reagents do not interfere with the efficiency of releasing, a washing step, or subsequent histochemical steps.

The non-polar organic solvent of the present composition is typically from about 1% to about 50% by volume of the releasing composition. Below the lower percent limit of non-polar organic solvent the capability of the composition to release an embedding medium is often significantly decreased. Above the upper limit of non-polar solvent an adverse affect on detergent solubility or water solubility occurs, which adversely affects the effectiveness of a subsequent aqueous wash. The upper limit of solvent can range through the upper limit values of 50 to 75%, while the lower limit of solvent can be selected from the lower limit values of 1 to 25%, to obtain a variety of ranges for embodiments of the invention.

The polar organic solvent of the present invention generally serves the purpose of dissolving the non-polar solvent, surfactant and, optionally, water. The polar organic solvent is soluble in water to the extent of at least 1 g per 100 g water, preferably 5 g per 100 g water, more preferably 10 g per 100 g water and most preferably the polar organic solvent is miscible with water. Polar organic solvents include ketones and lower alcohols, which include polyhydroxy alcohols and glycols, and lower ethers. Preferred alcohols are $C_1$ to $C_5$ alcohols. Most preferred are ethanol, ethylene glycol, isopropanol, propylene glycol and mixtures thereof. A preferred ketone solvent is typically $C_3$ to $C_5$ ketone. Most preferred ketone solvents are acetone and methyl ethyl ketone. Preferred ethers are $C_2$ to $C_6$ ethers. Particularly preferred polar organic solvents are selected from the group consisting of methanol, ethanol, isopropanol, butanol, tert-butanol, allyl alcohol, acetone, ethylene glycol and propylene glycol, and a mixture thereof. Acetonitrile and dimethylformamide are less preferred polar organic solvents. Furthermore, the polar organic solvent can be a mixture of polar organic solvents.

The polar organic solvent in the composition is typically from about 5% to about 50% by volume of the composition. The upper limit of this solvent can be selected from the range of upper limit values of 50 to 75%, while the lower limit of solvent can be selected from the range of lower limit values of 5 to 25%, to obtain a variety of ranges for embodiments of the invention. Preferably the amount is from about 10% to about 40%, more preferably from about 20% to about 35%, and most preferably from about 20% to about 30%. At what combination of components a particular composition is miscible or separates can readily be determined from a phase diagram showing phase separation for different relative amounts of the components of the solution/mixture.

Surfactants which find use in the present invention include cationic surfactants, anionic surfactants, non-ionic surfactants, and zwitterionic surfactants. A number of biological detergents (surfactants) are listed as such by Sigma Chemical Company in its catalog of Biochemicals and Reagents Life Science Research. The surfactant serves the purpose of a detergent, since it has both hydrophilic and hydrophobic properties. A surfactant for use in the invention is soluble in the solvent used in a composition of the invention. Preferred surfactants are detergents that are soluble in water, ethanol and acetone. Most preferred are those that do not substantially interfere with downstream histochemical analyses, which can be determined, for example, by histochemical staining using a solution containing the surfactant.

Surfactants that can be used in compositions of the invention include cationic surfactants of the formula

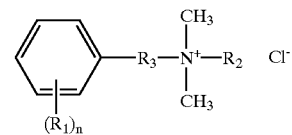

wherein $R_1$, is methyl, ethyl or propyl or isopropyl where n is 1 or 2; $R_2$, is an alkyl from $CH_3$ to $C_{30}H_{61}$ or a benzyl group; and $R_3$ is $(CH_2)_m$, where mn is from 1 to 10, or $R_3$ is $(OCH_2CH_2)$, where p is from 1 to 10. Cationic surfactants of this formula are soluble in the polar organic solvents. Many preferred embodiments of the invention contain the cationic surfactant benzalkonium chloride or benzethonium chloride. Additional cationic detergents, not necessarily of this formula, include dodecyltrimethylammonium bromide, benzyldimethylhexadecyl ammnonium chloride, cetiyphyridinium chloride, methylbenzethonium chloride, and 4-picoline dodecyl sulfate.

Other surfactants that can be used in the compositions of the invention include anionic surfactants having the formula

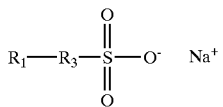

wherein $R_1$ is $C_6H_{13}$ to $C_{30}H_{61}$, and $R_3$ is O, $CH_2$ or phenyl group. Anionic surfactants of this formula are soluble in a polar organic solvent. Examples of anionic detergents, not necessarily having this formula, include alginic acid, caprylic acid, cholic acid, 1-decanesulfonic acid, deoxycholic acid, 1-dodecanesulfonic acid, N-lauroylsarcosine, and taurocholic acid. Other anionic synthetic non-soap detergents, which are represented by the water-soluble salts of organic sulfuric acid reaction products, have in their molecular structure an alkyl radical containing from about 8 to 22 carbon atoms and a radical selected from the group consisting of sulfonic acid and sulfuric acid ester radicals. Examples of these are the sodium or potassium alkyl sulfates, derived from tallow or coconut oil; sodium or potassium alkyl benzene sulfonates; sodium alkyl glyceryl ester sulfonates; sodium coconut oil fatty acid monoglyceride sulfonates and sulfates; sodium or potassium sales of sulfuric acid esters of the reaction product of one mole of a higher fatty alcohol and about 1 to 6 moles of ethylene oxide per molecule and in which the alkyl radicals contain from 8 to 12 carbon atoms; the reaction product of fatty acids esterified with isethionic acid and neutralized with sodium hydroxide, sodium or potassium salts of fatty acid amide of a methyl tauride; and sodium and potassium salts of $SO_3$-sulfonated $C_{10}$–$C_{24}$ α-olefins.

Further surfactants that can be used in compositions of the invention include non-ionic surfactants having the formula

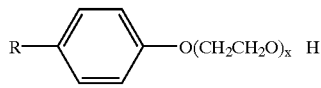

wherein R is a linear or branched C1 to C10 alkyl group and X is an integer from 5 to 40. Most preferably R is

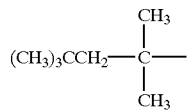

Non-ionic surfactants of this formula are soluble in polar organic solvents. Examples of nonionic detergents, not necessarily having this formula, include decanoyl-N-methylglucamide, diethylene glycol monopentyl ether, n-dodecyl P-D-glucopyranoside, polyoxyethylene esters of fatty acids (particularly $C_{12}$–$C_{20}$ fatty acids, (e.g., sold under the trade name Triton), ethylene oxide condensates of fatty alcohols e.g. sold under the name Lubrol), polyoxyethylene sorbitan fatty acid esters (e.g., sold under the trade name Tween), and sorbitan fatty acid esters (e.g., sold under the trade name Span). Nonionic synthetic detergents made by the condensation of alkaline oxide groups with an organic hydrophobic compound. Typical hydrophobic groups include condensation products of propylene oxide with propylene glycol, alkyl phenols, condensation product of propylene oxide and ethylene diamine, aliphatic alcohols having 8 to 22 carbon atoms, and amides of fatty acids. Also nonionic detergents such as amine oxides, phosphine oxides and sulfoxides having semipolar characteristics and be removed. Specific examples of long chain tertiary amine oxides include dimethyldodecylamine oxide and bis-(2-hydroxyethyl)dodecylamine. Specific examples of phosphine oxides are found in U.S. Pat. No. 3,304,263, and include dimethyldodecylphosphine oxide and dimethyl-(2-hydroxydodecyl) phosphine oxide. A preferred non-ionic detergent surfactant is Triton X-100, which is a trade name for a polyoxyethylene ester of fatty acids (particularly $C_{12}$–$C_{20}$ fatty acids).

Zwitterionic surfactants include known compounds of the formula N-alkyl-N, N, -dimethyl-3-ammonio-1-propanesulfonate. Examples of zwitterionic detergents include 3-[3-cholamidopropyl)-dimethylamrnmonio]-1] propanesulfonate (commonly abbreviated CHAPS), 3-[cholamidopropyl)-dimethylammonio]-2-hydroxy-1-propane sulfonate (generally abbreviated CHAPSO), N-dodecyl-N-dimethyl-3-ammonio-1-propane sulfonate, and lyso-α-phosphatidyl-choline.

The surfactant concentration in the composition of the present invention is typically from about 0.05% to about 50% by weight to volume, more commonly from about 0.5% to about 20% weight to volume, of the composition. Below the lower limit of surfactant concentration, poor solubility of wax (or releasing of the embedding medium) in the composition is observed. The upper limit of surfactant concentration is a primarily a factor of the selected surfactant's solubility limit.

Compositions of the invention can also contain water. Most preferably the amount of water in a selected composition is a saturating amount of water. Above this upper limit phase separation of the composition occurs. Because the compositions of the present invention can be used throughout a wide temperature range, the amount of water, and thus the concentrations of the remaining components of the composition, can vary widely. Typically the amount of water in the composition will range from about 0.5% to about 95% by volume. Where the composition is intended to be used at the lower end of the temperature range, the amount of water is less than about 30% and often less than about 10% by volume of the composition. Some embodiments of the invention, for example as exemplified in the Examples, have less than about 7% water, some have from about 0.5% to about 1.5% water, and still others have less than about 1% water by volume. Conversely, where the composition is intended to be used at the upper end of the temperature range, that is, at or near 100° C., the amount of water can be greater than about 50% and often greater than about 80% by volume of the composition. Some embodiments of the invention have more than about 70% water.

In some embodiments of the invention, the releasing compositions or the aqueous wash solutions contain buffer, salts or other reagents useful for solubilization of the embedding medium, washes, or subsequent histochernical steps, so long as such optional reagents do not interfere with the releasing capability of the composition, the efficiency of a washing step, or subsequent histochemical steps. Reagents useful for subsequent processing or histochemical steps include carboxylic acid esters, enzymes such as lipases, and nucleophilic reagents as described in U.S. Pat. No. 5,578, 452, which is incorporated herein by reference. Optional agents can serve to expose or enhance aldehyde-fixed tissue antigen(s) for histochemical staining. Additional optional reagents include anti-microbial agents and stabilizers that increase composition shelf life. Such anti-microbial agents and stabilizers are well known in the field. Such reagents are typically used at extremely small percentages, typically below 0.1%, compared to the main components. Preferred reagents are those that do not interfere with downstream histochemical analyses.

Each of the individual components of the compositions of the invention is either commercially obtainable, is isolated from natural sources using known procedures, or is synthesized according to known procedures. Compositions of the invention are typically prepared bysimple mixing of the components in the indicated amounts.

Methods of preparing histochemically reactive samples for sectioning via wax-or paraffin-impregnation are generally well known and easily carried out. The technique is quite simple and involves contacting a wax-embedded specimen with a releasing composition of the invention to solubilize the wax that impregnates the specimen prior to histochemical analyses, such as immunostaining. The method optionally comprises a further step of contacting the treated specimen immediately after releasing with an aqueous washing composition comprising a detergent to remove residual releasing composition.

Although the releasing method is typically and conveniently carried out in a range approximating room temperature, without the need for a temperature controlled bath, a more precise control of the required time for satisfactory releasing and washing is available if temperature-controlled baths are used. Heating decreases processing time. Operable temperatures overall range from about 5° to the boiling temperature of the solution, preferably from about 15° C. to the boiling temperature of the solution. In the lower end of the range, the method can be performed from near room temperature to near physiologic temperature, that is from about 20° C. to about 40° C. In this temperature range, the compositions will typically be selected with non-aqueous components in the upper ranges specified previously. In the upper end of the temperature range, the method can be performed from above physiologic temperature up to and including the boiling temperature of the composition, that is from about 40° C. to about 100° C. (or actual boiling temperature). In this temperature range, the compositions will typically be selected with non-aqueous components in the lower ranges specified previously, and the water will typically form a major portion of the releasing composition.

Typically the embedded specimen is contacted with a composition of the invention for a time sufficient to solubilize or release all or part of the embedding medium associated with the specimen. Factors influencing the time required for satisfactory results include temperature, thickness of the specimen section and composition of the embedding medium. Time for any particular specimen type is ordinarily determined empirically. However, five minutes of contact is usually sufficient for specimens of standard thickness mounted on microscope slides.

A sectioned specimen, typically affixed to a microscope slide, is contacted with a composition of the invention in any number of ways. Preferably, the specimen is immersed in a bath containing the composition, or alternatively an amount of composition sufficient to solubilize the wax can be placed on the specimen such that the specimen is covered by the composition. After sufficient time of contact has elapsed for releasing to occur, the specimen is removed from contact with the composition, and excess composition is removed, or otherwise eliminated, from the specimen, for example by draining, blotting or blowing. Optionally, a second or even a further releasing step or steps are performed, preferably with fresh releasing composition, to further assure removal or elimination of wax from the specimen.

The invention decreases or eliminates the requirement of alcohol baths for post-releasing washes, and post-releasing washes are not always required with compositions of the invention. If such a step proves desirable (because of a particularly sensitive immunostaining procedure, for example) the treated specimen can be contacted with an aqueous wash composition of the invention which comprises a detergent. A preferred wash solution comprises a buffer and a detergent. Preferably the detergent is non-ionic. A preferred buffer/detergent wash solution is phosphate buffered saline with about 1% nonionic surfactant polyoxyethylene ester such as BRIJ-35 (trade name for the nonionic surfactant polyoxyethylene glycol dodecyl ester or polyoxyethylene (23) lauryl ester). Typically the amount of detergent is from about 0.1% to about 5% (weight to volume), preferably from about 0.1% to 2%, and most preferably about 1%. The pH of the wash composition can range from about 2 to about 12, preferably from about 5 to about 8, more preferably from about 7.2 to about 7.6, and more preferably 7.4 to about 7.5. The pH is most preferably neutral to avoid adversely affecting downstream histochemical, particularly imniunochemical, analyses.

A preferred buffer is one which does not interfere with downstream analyses and/or can be readily removed with a subsequent aqueous wash or blowing. Phosphate buffered saline or Tris-containing buffers are examples of preferred buffers. Washing can occur in any number of ways, including immersion in a wash bath, flowing wash solution over the specimen, diffusing or permeating the wash solution throughout the specimen, or blowing. Wash time is ordinarily determined empirically; however, five minutes is usually sufficient. Multiple rinses and larger amounts of washing solution can be used to achieve increased removal of releasing solution. A single wash is sufficient for most purposes; however, a second wash is preferred if removal is not sufficient. Optionally, the specimen is finally washed or rinsed in water. A water wash of 3 minutes is usually sufficient for the most rigorous conditions. After washing the specimen is then ready for histochemical or other analyses.

The compositions of the invention, including the wash solutions, are also compatible with automated staining systems and devices, as described, for example, in U.S. Pat. Nos. 5,439,649 and 5,948,359, each of which are hereby incorporated by reference. Typically, such devices will comprise means for performing a predetermined sequence of operations under a predetermined set of conditions for histochemical analysis. Representative of such a device and system is the OptiMax™ Automated Immunostainer, BioGenex Laboratories San Ramon, Calif. In such automated histochemical analysis, previously treated slides can be provided to the automated stainer or an automated stainer can be provided with compositions of the invention to allow automated releasing of the embedded specimens prior to automated analyses.

Although preferred surfactants and other components used in a releasing solution of the invention are those that do not typically interfere with downstream analyses, particularly at the residual levels remaining on the specimen after the wash procedures, methods known in the art may be applied to enhance surfactant (or other component) removal should residual surfactant (or other component) cause problems in downstream analyses. For residual surfactant removal soluble compounds known to bind a surfactant may be included in an aqueous wash solution. For example, cyclodextrins are known to bind certain surfactants (U.S. Pat. No. 5,032,503) and may be included in a wash solution. Protein, such as bovine serum albumin, can be included in a wash solution to bind and remove residual surfactant. In one preferred embodiment, a surfactant that does not interfere with the downstream analyses, but that can displace the residual surfactant, can be used in an aqueous wash solution. This displacing surfactant is preferably easily removed with a water wash. Polyoxyethylene alkyl ester type non-ionic surfactants are a preferred wash surfactant. BRIJ-35 (trade name for polyoxyethylene glycol dodecyl ester) is an example of one such surfactant.

Also provided is a kit for releasing the embedding medium from an embedded specimen. The kit comprises a container of releasing composition and containers of (1) histochemically reactive staining reagents or (2) an aqueous wash solution for removing, or otherwise eliminating, residual releasing solution. The containers are typically located in a receptacle specifically adapted to hold them. Preferably the wash solution contains a buffer and a detergent. In one embodiment the histochemically reactive staining reagent is an immunostaining reagent. In another embodiment the histochemically reactive staining reagent is an in situ hybridization reagent. The kit can be a component of a larger kit for histochemical analyses, such as in a kit for use with automated immnunostainers. Any of the other reagents described herein can be used in the kit in combination with the specified components.

The compositions and methods of the invention are suitable for use in a variety of histochemical applications, particularly immunochemical staining using special stains and other classical stains. In situ hybridization with nucleic acid probes is another particularly pertinent use compatible with compositions and methods of the invention.

The present invention eliminates or reduces the use of certain toxic organic solvents (e.g. xylene, xylene substitutes, alcohols, and the like) in immunohistologicai laboratories. The compositions and methodology described herein effectively removes, or otherwise eliminates, paraffin and other waxes residues from tissue sections and has no adverse effect on the quality of tissue sections prepared for histochemical analysis. Application of this releasing methodology can be extended to other applications where removal of paraffin and other waxes from tissue sections are necessary. In preferred embodiments using isoparaffins; the compositions have a very low order of acute toxicity, being practically non-toxic by oral, dermal and inhalation routes. In addition the compositions allow a method of releasing that eliminates the use of graded alcohol washes. Accordingly, the embodiments of the present invention meet the need of providing compositions and methods that minimize dangers to the user and minimize the creation of hazardous waste.

The invention now being generally described, the same will be better understood by reference to the following detailed examples which are provided for illustration and are not to be considered as limiting the invention unless so specified.

EXPERIMENTAL

In the experimental disclosure which follows, all weights are given in grams (g), milligrams (mg), micrograms ($\mu$g), nanograms (ng), or picograms (pg), all amounts are given in moles (mol), millimoles (mmol), micromoles ($\mu$mol), nanomoles (nmol), picomoles (pmol), or femtomoles (fmol), all concentrations are given as percent by volume (%), proportion by volume (v:v), molar (M), millimolar (mM), micromolar ($\mu$M), nanomolar (nM), picomolar (pM), femtomolar (fM), or normal (N), all volumes are given in liters (L), milliliters (mL), or microliters ($\mu$L), and linear measurements are given in millimeters (mm), or nanometers (nm) unless otherwise indicated.

The following examples demonstrate the practice of the present invention in preparing embedded tissue specimens for histochemical analyses.

Example 1

Releasing Compositions

The following examples of releasing compositions are presented by way of illustration of embodiments of the invention and not intended to limit the invention.

Composition 1 is prepared by. mixing reagent alcohol (275 mL; a premixed solution of 90% v/v anhydrous ethyl alcohol, 5% v/v methyl alcohol and 5% v/v isopropyl alcohol), limonene (100 mL), water (25 mL) and benzalkonium (20 g).

Composition 2 is prepared by mixing. reagent alcohol (50 mL), limonene (50 mL) and benzalkonium (10 g).

Composition 3 is prepared by mixing reagent alcohol (50 mL), isoparaffin (50mL), water (0.6 mL) and benzalkonium (15 g).

Composition 4 is prepared by mixing reagent alcohol (100 mL), isoparaffin (50 mL), mineral spirits (50 mL) and benzalkonium (15 g).

Composition 5 is prepared by mixing reagent alcohol (50 mL), isoparaffin (50 mL), water (0.9 mL) and Triton-X100 (10 g).

Composition 6 is prepared by mixing reagent alcohol (65 mL), isoparaffin (45 mL), water (0.5 mL) and BRIJ-35 (1.0 g).

Composition 7 is prepared by mixing citric acid (0.48 g), reagent alcohol (20 mL), isoparaffin (20 mL), water (1000 mL) and Triton-X100 (10 mL), then adjusting the pH to 8.5 with 20% NaOH solution.

Composition 8 is prepared by mixing citric acid (0.48 g), reagent alcohol (40 mL), water (1000 mL), Triton-X100 (10 mL), and BRIJ-35 (1.0 g), then adjusting the pH to 7.4 with 20% NaOH solution.

One embodiment of the isoparaffin (isoparaffinic hydrocarbon solvent) used in the compositions of this example is available as Micro-Clear, a trade name of Micron Diagnostics, Inc., for its isoparaffinic hydrocarbon solvent.

Example 2

Manual Releasing of Embedding Media

Releasing embedding media from slidemounted tissue specimens using each of Compositions 1–8 of Example 1 individually is performed prior to histological analysis. Humain or animal tissues used in this Example include skin, pancreas, tonsil, spleen, lung, breast prostate, colon carcinoma, melanoma and astrocytoma.

Example 2A

Releasing of Embedding Media at Low Temperature

Each slide containing slide-mounted, paraffin-embedded tissue sections is immersed in a glass-jar containing 60 mL of one of the releasing Compositions 1–6. After five minutes at 25° C., the releasing composition is decanted and replaced with fresh releasing composition and the slides are treated for an additional five minutes.

Optionally, a third five minute releasing treatment can also be performed. Immediately after releasing, slides are rinsed in an aqueous wash composition containing PBS with 1% BRIJ-35 for five minutes, rinsed in tap water for three minutes, and used for histochemical analysis.

Example 2B

Releasing of Embedding Media at High Temperature

Each slide containing slide-mounted, paraffin-embedded tissue sections is immersed in a glassjar containing 60 mL of one of the releasing Compositions 7–8. After five minutes at 100° C., the releasing composition is decanted. Optionally, a second or third five minute releasing treatment can also be performed. Immediately after releasing, slides are rinsed in an aqueous wash composition containing PBS with 1% BRIJ-35 for five minutes, rinsed in tap water for three minutes, and used for manual or automated histochemical analysis.

Example 3

Automated Releasing of Embedding Media

Releasing embedding media from slide-mounted tissue specimens using Compositions 1–6 of Example 1 individually is performed as one phase of automated histochemical analysis, generally as follows. Human or animal tissues used in this Example include skin, pancreas, tonsil, spleen, lung, breast prostate, colon carcinoma, melanoma and astrocytoma.

Each slide containing slide-mounted, paraffin-embedded tissue sections is loaded onto a slide rack of an automated, consolidated histochemical staining apparatus (e.g. Opti-Max™ Automated Immunostainer, BioGenex Laboratories San Ramon, Calif.) and the releasing procedure is implemented in accordance with the instructions of the manufacturer. In this regard, the reagent-dispensing head dispenses 2 to 3 mL of one of the releasing Compositions 1–6 on each slide. The slide-mounted tissue sections are incubated with the releasing composition for three minutes, the releasing composition is removed by the air orifice with blowing action and, without a rinse phase, replaced with 2 to 3 mL of fresh releasing composition for a further three minutes.

Thereafter, the releasing composition is again removed by the air orifice, and the slides are subjected to a series of wash solution rinses, first with one to three cycles of deionized water, then with one to three cycles of a buffer solution.

Typically, the settings for cycles and incubation times are selected as the default settings in accordance with the protocols established by the manufacturer; alternatively, the number and durations of the incubations and rinse cycles can be adjusted according to the preference of the user.

Example 4

Releasing with Xylene

A widely used, standard deparaffinization protocol involving xylene is performed as a control. Slide-mounted, paraffin-embedded tissue specimens are immersed in 100% xylene for five minutes followed by two changes in fresh 100% xylene for five minutes each.

Thereafter, the slides are immersed in a bath of 100% alcohol twice for three rminutes each time. The slides are then immersed sequentially in baths of 95% alcohol, 85% alcohol and then 75% alcohol for three minutes in each bath. The slides are finally rinsed in tap water for three minutes and used for histochemical analysis.

A further series of slides are prepared following this protocol, but substituting either limonene or Micro-Clear for xylene.

Example 5

Effectiveness of Paraffin Removal

The released slides prepared as in Examples 2, 3 and 4 are examined after hematoxylin and eosin (H&E) staining for effectiveness of paraffin removal or elimination. After the slides are released with releasing Compositions 1–6 and washed with aqueous wash composition, no paraffin residue is detected on the specimens or on other locations on the slides. In addition, no paraffin residue is detected on specimens or slides cleared with the control procedure using xylene and hydrated with graded alcohols and water followed by H&E staining. There is no discernible difference in effectiveness for paraffin removal among xylene, limonene, isoparaffin, and releasing Compositions 1–8 of Example 1.

Example 6

Effect of Releasing Solvents on Immunohistochemistry Staining

Normal or tumorous animal tissues including skin, pancreas, tonsil, spleen, lung, breast, prostate, colon carcinoma, melanoma and astrocytoma, are stained with corresponding monoclonal antibodies to determine the effects of the present releasing compositions on immunohistochemical staining. Xylene treated tissue specimen slides are used as standard controls.

Slides containing tissue specimens released as described in Examples 2 and 3 are examined for compatibility to immunohistological analyses. Released slides are covered in Block Solution I (a trade name of BioGenex Laboratories, San Ramon, Calif., for a solution of PBS and 3% hydrogen peroxide) for ten minutes. Each slide is then rinsed in PBS twice, for five minutes each time. Primary antibodies (200 $\mu$L; obtained from BioGenex Laboratories, San Ramon, Calif., under the trade name Ready to Use Antibodies) are incubated with their respective tissue specimens for 30 minutes or two hours, according to individual staining protocols provided by the supplier. The following monoclonal antibodies are used in immnunohistochemistry: anti-human cytokeratin cocktail, anti-NSE, anti-insulin, anti-LCA, anti-kappa chain, anti-Q-band, anti-L26, anti-factor VIII, anti-CEA, anti-p53, anti-Cerb-2, anti-PR, anti-vimentin, anti-PSA, anti-HMB45, anti-S-100 and anti-GFAP. The slides are then washed in PBS three times, for five minutes each time. After a 20 minute incubation with biotinylated secondary antibodies (available under the trade name Super Sensitive Link from BioGenex Laboratories, San Ramon, Calif.), the slides are washed in PBS three times, for five minutes each time. The slides are then incubated with a stock solution of peroxidase-conjugated streptavidin (available under the trade name Super Sensitive Label from BioGenex Laboratories, San Ramon, Calif.) for 20 minutes and washed three times in PBS. Desirably, the slides can be stained utilizing stains fro BioGenex Laboratories in the OptiMaxM Plus system. The chromogenic reaction is carried out using AEC (3-amino-9-ethylcarbozole) for peroxidase and Fast Red for alkaline phosphatase. After color development, each slide is rinsed in tap water, counter-stained, mounted and examined by light microscopy.

Intensity of immunostaining reactivity is evaluated by a light-microscope. There is found to be no detectable difference in immunostaining intensity among slide-mounted specimens released with releasing Compositions 1–8, and specimens treated with the control with xylene.

All patents and patent applications cited in this specification are hereby incorporated by reference as if they had been specifically and individually indicated to be incorporated by reference.

Although the foregoing invention has been described in some detail by way of illustration and example for purposes of clarity and understanding, it will be apparent to those of ordinary skill in the art in light of the disclosure that certain changes and modifications may be made thereto without departing from the spirit or scope of the appended claims.

What is claimed is:

1. A method for releasing the embedding medium from an embedded histochemically reactive tissue specimen, said method comprising contacting said embedded tissue specimen with a releasing composition comprising a non-polar organic solvent, a polar organic solvent, a surfactant, and water, under conditions sufficient to release a sufficient portion of the embedding medium associated with the histochemically reactive tissue specimen to permit analysis without substantial adverse effect on the histochemical reactivity of the specimen.

2. The method of claim 1 wherein the conditions for contacting said embedded tissue specimen comprise incubating said composition at a temperature in the range of approximately 10° C. to approximately 100 ° C. for a time sufficient to release a substantial portion of the embedding medium associated with the tissue specimen.

3. The method of claim 1 which further comprises the step of washing said tissue specimen after said contacting step with an aqueous wash solution under conditions sufficient to remove, or otherwise eliminate, at least a portion of any residual releasing composition from said tissue specimen.

4. An automated method for releasing the embedding medium from an embedded histochemically reactive tissue specimen, said automated method comprising (a) providing an apparatus comprising means for performing a predetermined sequence of operations under a predetermined set of conditions for histochemical analysis which includes at least the step of releasing the embedding medium from an embedded histochemically reactive tissue specimen;
and
(b) contacting said embedded tissue specimen under the control of said apparatus with a releasing composition comprising a non-polar organic solvent, a polar organic solvent, a surfactant, and water, under conditions sufficient to release a sufficient portion of the embedding medium associated with the histochemically reactive tissue specimen to permit analysis without substantial adverse effect on the histochemical reactivity of the specimen.

5. The method of claim 4 wherein the conditions imposed by said apparatus for contacting said embedded tissue specimen comprise incubating said composition at a temperature in the range of approximately 10° C. to approximately 100° C. for a time sufficient to release a substantial portion of the embedding medium associated with the tissue specimen.

6. The method of claim 4 which further comprises the step of washing said tissue specimen under the control of said apparatus after said contacting step with an aqueous wash solution under conditions sufficient to remove, or otherwise eliminate, at least a portion of any residual releasing composition from said tissue specimen.

7. The method of claim 1, wherein the non-polar organic solvent comprises at least one aromatic hydrocarbon, terpene or isopararaffinic hydrocarbon.

8. The method of claim 1, wherein the non-polar organic solvent is from about 1% to about 50% by volume of said composition.

9. The method of claim 1, wherein the polar organic solvent comprises at least one alcohol, ketone, or other.

10. The method of claim 1, wherein the polar organic solvent is from about 1% to about 50% by volume of said composition.

11. The method of claim 1, wherein the surfactant comprises at least one cationic surfactant having the formula

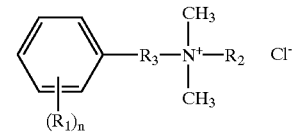

wherein $R_1$ is methyl, ethyl or propyl or isopropyl where n is 1 or 2; $R_2$ is an alkyl from $CH_2$ to $C_{30}H_{61}$ or benzyl group; and $R_3$ is $(CH_2)_m$ where m is from 1 to 10, or $R_3$ is $(OCH_2CH_2)_p$ where p is from 1 to 10.

12. The method of claim 1, wherein the surfactant comprises at least on anionic surfactant having the formula

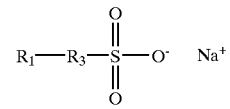

wherein $R_1$ is $C_6H_{11}$ to $C_{30}H_{61}$ and $R_3$ is $CH_2$ or a phenyl group.

13. The method of claim 1, wherein the surfactant comprises at least one non-ionic surfactant having the formula

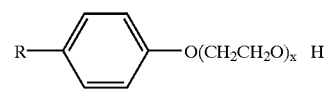

wherein R is a linear or branched C1 to C10 alkyl group and X is from 5 to 40.

14. The method of claim 4, wherein the non-polar organic solvent comprises at least one aromatic hydrocarbon, terpene or isoparaffinic hydrocarbon.

15. The method of claim 4, the non-polar organic solvent is from about 1% to about 50% by volume of said composition.

16. The method of claim 4, wherein the polar organic solvent comprises at least one alcohol, ketone, or ether.

17. The method of claim 4, wherein the polar organic solvent is from about 1% to about 50% by volume of said composition.

18. The method of claim 4, wherein the surfactant comprises at least one cationic surfactant having the formula

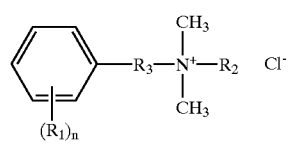

wherein $R_1$ is methyl, ethyl or propyl or isopropyl where n is 1 or 2; $R_2$ is an alkyl from $CH_3$ to $C_{30}H_{61}$ or a benzyl group; and $R_3$ is $(CH_2)$ where m is from 1 to 10, $R_1$ is $(OCH_2CH_2)_p$ where p is from 1 to 10.

19. The method of claim 4, wherein the surfactant comprises at least on anionic surfactant having the formula

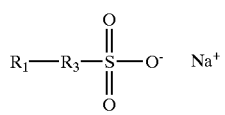

wherein $R_1$ is $C_6H_{13}$ to $C_{30}H_{61}$ and $R_3$ is $CH_2$ or a phenyl group.

20. The method of claim 4, wherein the surfactant surfactant comprises at least one non-ionic surfactant having the formula

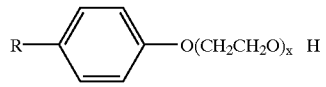

wherein R is a linear or branched C1 to C10 alkyl group and X is from 5 to 40.

* * * * *